United States Patent
Newby et al.

(10) Patent No.: US 10,295,445 B2
(45) Date of Patent: May 21, 2019

(54) CONTAINER SYSTEM FOR TISSUE STABILIZATION FOR MOLECULAR AND HISTOPATHOLOGY DIAGNOSTICS

(71) Applicant: Becton, Dickinson and Company, Franklin Lakes, NJ (US)

(72) Inventors: C. Mark Newby, Tuxedo, NY (US); Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/176,717

(22) Filed: Jun. 8, 2016

(65) Prior Publication Data

US 2016/0282238 A1   Sep. 29, 2016

Related U.S. Application Data

(63) Continuation of application No. 12/257,073, filed on Oct. 23, 2008, now Pat. No. 9,389,153.

(Continued)

(51) Int. Cl.
    *B01L 3/00* (2006.01)
    *G01N 1/31* (2006.01)
    *G01N 1/30* (2006.01)

(52) U.S. Cl.
    CPC .............. *G01N 1/31* (2013.01); *B01L 3/502* (2013.01); *B01L 3/508* (2013.01); *G01N 1/30* (2013.01);

(Continued)

(58) Field of Classification Search
    CPC ..................................................... G01N 1/31
    (Continued)

(56) References Cited

U.S. PATENT DOCUMENTS

| 4,034,884 A | 7/1977 | White |
| 4,076,592 A | 2/1978 | Bradley |

(Continued)

FOREIGN PATENT DOCUMENTS

| DE | 20201894 U1 | 5/2002 |
| EP | 0332753 A1 | 9/1989 |

(Continued)

OTHER PUBLICATIONS

Chromtech (2005 catalog p. 319).
U.S. Appl. No. 12/257,057.
U.S. Appl. No. 12/257,134.

*Primary Examiner* — Kevin Joyner
*Assistant Examiner* — Holly M Mull
(74) *Attorney, Agent, or Firm* — The Webb Law Firm

(57) ABSTRACT

A system for storing a biological sample for transfer between two different environments is provided. The system includes a first container defining a first container interior, and a second container defining a second container interior. A first closure is provided for enclosing the open end of the first container, with the first closure adapted to receive a sample holder. A second closure is also provided for enclosing the open end of the second container. The first container is adapted to removably receive the sample holder therein when the first closure encloses the open end of the first container, and the second container is adapted to subsequently receive the same sample holder therein when the first closure encloses the open end of the second container.

8 Claims, 10 Drawing Sheets

Related U.S. Application Data

(60) Provisional application No. 60/982,025, filed on Oct. 23, 2007.

(52) U.S. Cl.
CPC ... *B01L 2200/025* (2013.01); *B01L 2200/026* (2013.01); *B01L 2200/14* (2013.01); *B01L 2300/021* (2013.01); *B01L 2300/041* (2013.01); *B01L 2300/0609* (2013.01); *B01L 2300/0858* (2013.01); *G01N 2001/315* (2013.01)

(58) Field of Classification Search
USPC ....................................... 435/307.1
See application file for complete search history.

(56) References Cited

U.S. PATENT DOCUMENTS

| | | |
|---|---|---|
| 4,094,483 A | 6/1978 | Busch |
| 4,220,252 A | 9/1980 | Beall et al. |
| 4,286,633 A * | 9/1981 | Herr ............... B65D 50/041 141/24 |
| 4,416,984 A | 11/1983 | Wheeler, Jr. |
| 4,903,869 A | 2/1990 | McKenna |
| 5,455,180 A | 10/1995 | Reid |
| 6,207,408 B1 | 3/2001 | Essenfeld et al. |
| 6,875,583 B2 | 4/2005 | Giberson et al. |
| 6,899,850 B2 | 5/2005 | Haywood et al. |
| 7,147,826 B2 | 12/2006 | Haywood et al. |
| 8,449,844 B2 | 5/2013 | Wilkinson et al. |
| 8,813,954 B2 | 8/2014 | Newby |
| 2002/0048819 A1 | 4/2002 | Alley |
| 2003/0086830 A1 | 5/2003 | Haywood et al. |
| 2004/0038269 A1 | 2/2004 | Bimboim |
| 2004/0184954 A1 | 9/2004 | Guo et al. |
| 2005/0163660 A1 | 7/2005 | Wang |
| 2006/0205682 A1* | 9/2006 | Roberts ............... A61K 31/505 514/28 |
| 2006/0245977 A1 | 11/2006 | Bodner |
| 2008/0025877 A1 | 1/2008 | Alley |
| 2009/0100944 A1 | 4/2009 | Newby |
| 2009/0104692 A1 | 4/2009 | Bartfeld et al. |
| 2009/0105611 A1 | 4/2009 | Wilkinson et al. |
| 2009/0183581 A1 | 7/2009 | Wilkinson et al. |
| 2010/0009349 A1* | 1/2010 | Hollander ............... B01L 3/508 435/6.17 |

FOREIGN PATENT DOCUMENTS

| | | |
|---|---|---|
| EP | 1804045 A1 | 7/2007 |
| FR | 2612297 A1 | 9/1988 |
| GB | 1234044 A | 6/1971 |
| JP | 59113886 A | 6/1984 |
| JP | 06078746 A | 3/1994 |
| JP | 10281953 A | 10/1998 |
| JP | 2000510703 A | 8/2000 |
| JP | 2001194365 A | 7/2001 |
| JP | 200357232 A | 2/2003 |
| JP | 4965889 B2 | 7/2012 |
| WO | 7901131 A1 | 12/1979 |
| WO | 03031065 A1 | 4/2003 |
| WO | 03044488 A1 | 5/2003 |
| WO | 2006041297 A2 | 4/2006 |
| WO | 2007014741 A2 | 2/2007 |
| WO | 2007016935 A1 | 2/2007 |
| WO | 2008040812 A1 | 4/2008 |

\* cited by examiner

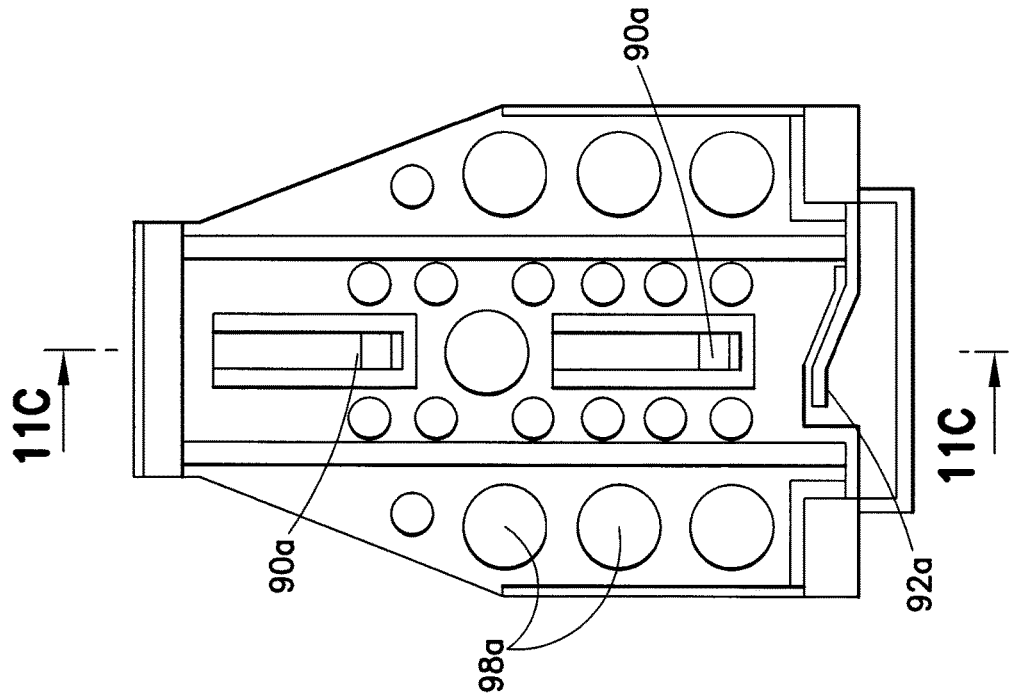
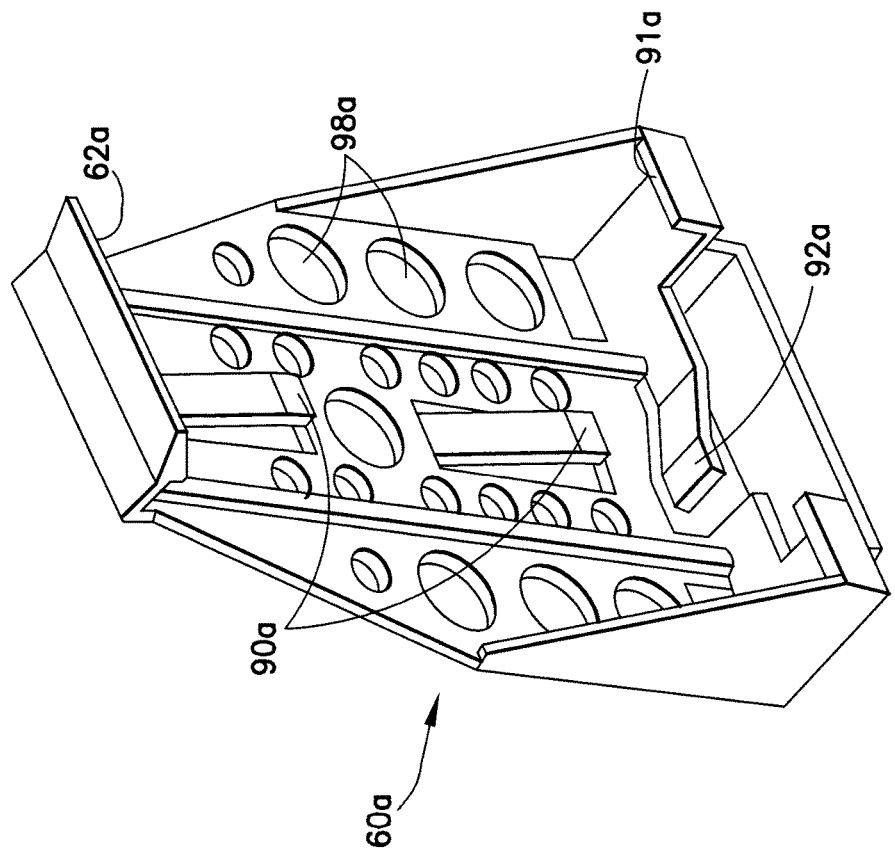

CONTAINER SYSTEM FOR TISSUE STABILIZATION FOR MOLECULAR AND HISTOPATHOLOGY DIAGNOSTICS

CROSS REFERENCE TO RELATED APPLICATION

This application is a continuation application of U.S. patent application Ser. No. 12/257,073, filed Oct. 23, 2008, entitled "Container System for Tissue Stabilization for Molecular and Histopathology Diagnostics", which claims priority to U.S. Provisional Patent Application No. 60/982,025, filed Oct. 23, 2007, entitled "Container System for Tissue Stabilization for Molecular and Histopathology Diagnostics", the entire disclosures of each of which are herein incorporated by reference.

BACKGROUND OF THE INVENTION

Field of the Invention

The present invention relates to a container system for storing a biological tissue sample. More particularly, the present invention is directed to a two container system for storing a biological tissue sample in a reagent or, if so desired, in multiple reagents.

Description of Related Art

Biological samples are often obtained by a researcher or clinician for diagnostic evaluation to determine the presence of certain diseases and to determine an appropriate treatment for the disease. These samples are also obtained for molecular diagnostic and nucleic acid analysis, particularly RNA and DNA analysis, which have become common place in research for the treatment of numerous diseases. An essential requirement for accurate RNA and DNA analysis is the presence of high quality and intact RNA and DNA within the biological sample.

Often times, the histologic or cytologic analysis will be performed immediately after the sample is removed from the patient or source to avoid molecular changes that may occur during storage. These changes, such as gene transcription, result from the degradation of the nucleic acids within the sample caused by exposure of an untreated sample to certain environmental stresses. However, analysis of the sample immediately after the sample is collected is often impossible or impractical. Therefore, it is necessary to provide a system for storing a sample under controlled conditions for a certain period of time while maintaining the structural and molecular integrity of the sample.

Traditionally, one way of accomplishing this storage was by submerging the sample in a single fixative reagent. A typical fixative reagent is 10 percent (%) formalin but may also include water miscible alcohols, ethanol/acetone mixtures, and ethanol/acetic acid mixtures. The containers used for such storage were generally composed of a single integral cavity which could house an effective volume of reagent to treat a particular biological sample. The biological sample, along with the reagent, would be placed in the container, the container would be closed, and the sample could then be stored and transported while being preserved by the fixative agent. An example of such a container can be seen in U.S. Pat. No. 7,147,826 to Haywood et al. These containers have experienced some success in the industry, but are subject to certain limitations.

SUMMARY OF THE INVENTION

In one embodiment, the present invention provides a kit of parts including a first container having a closed end, an open end, and a sidewall extending between the closed end and the open end defining a first container interior. The kit includes a second container having a closed end, an open end, and a sidewall extending between the closed end and the open end defining a second container interior. The kit further includes a first closure for enclosing the open end of the first container in a first instance and for enclosing the open end of the second container in a second instance, with the first closure adapted to receive a sample holder. The kit further includes a second closure for enclosing the open end of the second container. The first container interior is adapted to removably receive the sample holder therein when the first closure encloses the open end of the first container. The second container interior is adapted to subsequently receive the same sample holder therein when the first closure encloses the open end of the second container.

Optionally, the sample holder includes a closable housing defining an internal cavity for holding a biological sample. The housing may include a plurality of fluid openings adapted for allowing fluid contained within at least one of the first chamber and the second chamber to pass into the internal cavity. In a further configuration, the sample holder is a histology cassette. The sample holder may be rotatable with respect to the first closure.

In a further configuration, at least a portion of the first closure and at least a portion of the first container are adapted for threaded engagement therebetween. Optionally, the second closure is a removable membrane. The first closure may be engageable with the second container to enclose the open end of the second container. At least a portion of the first closure and at least a portion of the second container may be adapted for threaded engagement therebetween. The first closure may be engageable with the open end of the first container, and the first closure may be subsequently engageable with the open end of the second container.

Furthermore, at least one of the first container and the second container may include a visual indicator to differentiate the first container from the second container. In a further configuration, the interior of the first container defines a first intended fill volume and the interior of the second container defines a second intended fill volume, with the second intended fill volume being different from the first intended fill volume.

In another embodiment of the present invention, a system for storing and preserving a biological sample includes a first container having a closed end, an open end, and a sidewall extending between the closed end and the open end defining a first container interior. The system includes a second container having a closed end, an open end, and a sidewall extending between the closed end and the open end defining a second container interior. The system also includes a first closure for enclosing the open end of the first container. The first closure has a bottom surface adapted to receive a sample holder. The system further includes a second closure for enclosing the open end of the second container. A first solution is disposed within the first container, and a second solution is disposed within the second container, with the first and second solutions being different. The first closure is adapted to dispose the sample holder within the first container interior when the first closure encloses the open end of the first container, and the first closure is adapted to subsequently dispose the sample holder within the second container interior when the first closure encloses the open end of the second container.

The sample holder may include a closable housing defining an internal cavity for holding a biological sample, with the housing having a plurality of fluid openings adapted for allowing fluid contained within at least one of the first chamber and the second chamber to pass into the internal cavity. In a further configuration, the sample holder is a histology cassette. Optionally, the system is rotatable with respect to the first closure. In yet a further configuration, the second closure is a removable membrane.

In another embodiment of the present invention, an assembly for storing and preserving a biological sample includes a container having a closed end, an open end, and a sidewall extending between the closed end and the open end defining a container interior. A portion of the container interior defines a sample holder cavity. The assembly also includes a closure for enclosing the open end of the container. A platform adapted to receive a sample holder is rotatably engaged with the closure. The sample holder cavity is adapted to receive the sample holder therein when the closure is engaged with the open end of the container.

In one configuration, the closure is transitionable from a disengagement position in which the closure is disengaged from the open end of the container, to an engagement position in which the closure encloses the open end of the container. In one particular configuration, the platform must be aligned with the sample holder cavity in order to allow transition of the closure from the disengagement position to the engagement position. Optionally, the orientation of the platform with respect to the container interior remains substantially fixed during rotation of the closure with respect to the container.

In yet another embodiment of the present invention, a method of storing and preserving a biological sample includes the step of providing a first container having a closed end, an open end, and a sidewall extending between the closed end and the open end defining a first container interior with a first solution disposed within the first container interior. The method also includes the step of providing a second container having a closed end, an open end, and a sidewall extending between the closed end and the open end defining a second container interior, with a second solution disposed within the second container interior. The second solution is different than the first solution. The method also includes the step of engaging a first closure with the first container for enclosing the open end of the first container. The first closure includes a sample holder housing a biological sample therein, and is adapted for submerging the biological sample within the first solution. The method further includes the step of engaging the first closure with the second container for enclosing the open end of the second container. The first closure further adapted for submerging the biological sample within the second solution after submerging the biological sample within the first solution.

Further details and advantages of the invention will become clear upon reading the following detailed description in conjunction with the accompanying drawing figures, wherein like parts are designated with like reference numerals throughout.

BRIEF DESCRIPTION OF THE DRAWINGS

FIG. 11A is a perspective view of an alternate embodiment of a platform for use in connection with the present invention.

FIG. 11B is a front view of the platform of FIG. 11A.

DETAILED DESCRIPTION OF PREFERRED EMBODIMENTS

Figure 1:
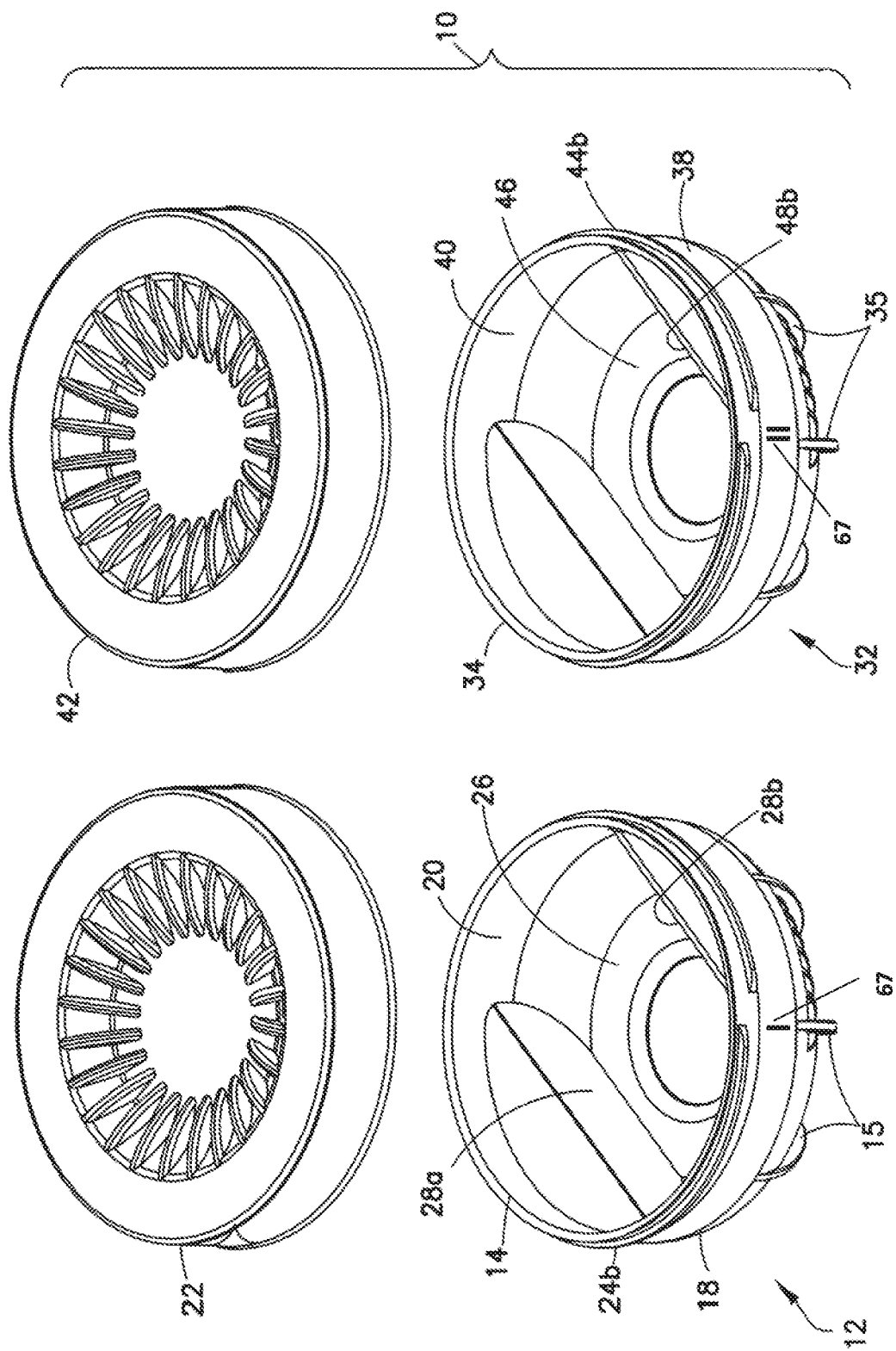
FIG. 1 is a perspective view of the container system pursuant to one embodiment of the invention.

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

The container system of the present invention allows for storage of a biological sample, such as a tissue sample for molecular and histology diagnostics, and in particular histopathology testing. In particular, the container system includes a plurality of containers for containing various reagent solutions therein, and adapted for containing a sample holder containing a tissue sample therein, such that the tissue sample can be transferred between one or more of the plurality of containers. Such transfer may be accomplished by connecting the tissue sample holder to the closure of one of the containers, with all of the plurality of containers adapted to receive the closure therein, with the tissue sample holder attached thereto.

For example, the container system may include a first container and a second container with each container comprised of an open end, a closed end, and a sidewall extending between the open end and the closed end defining a container interior. Accordingly, a liquid medium may be contained in at least one of the containers, such as the second container. In this manner, a tissue sample contained in, for example, the first container may be handled or processed prior to contacting the tissue with the solution in the second container. As will be discussed in greater detail herein, in one embodiment of the invention, the first container may be empty, representing a storage container, and the second container may include a liquid medium, such as a reagent in the form of a tissue fixative solution for fixing a sample for histopathology diagnostics. In this manner, the two containers may be provided as a sampling kit, and a tissue sample may be placed within the first container, and when desired, the sample may be thereafter repositioned to the second container so as to place the tissue sample in fluid contact with the solution within the second container. Alternatively, the first container may include a reagent therein with the second container being empty, such that the tissue sample may be first placed in the first container including the reagent, and after the tissue sample is in contact with the reagent for a desired time period, the tissue sample may be thereafter transferred to the empty second container for storage and further analysis.

In a further embodiment of the invention, the first container may contain a first solution or reagent, such as a tissue fixative solution, and the second container may contain a second solution or reagent, such as a nucleic acid stabilization solution, such that a tissue sample may be placed in the first container in fluid contact with the first solution for a desired time period, after which time the tissue sample may be repositioned to the second container so as to place the tissue sample in fluid contact with the solution within the second container. Accordingly, the system of the present invention provides a mechanism for storing a particular sample in two distinct environments. The embodiments described herein are representative of container units and systems capable of use in any of these manners.

Figure 7A:
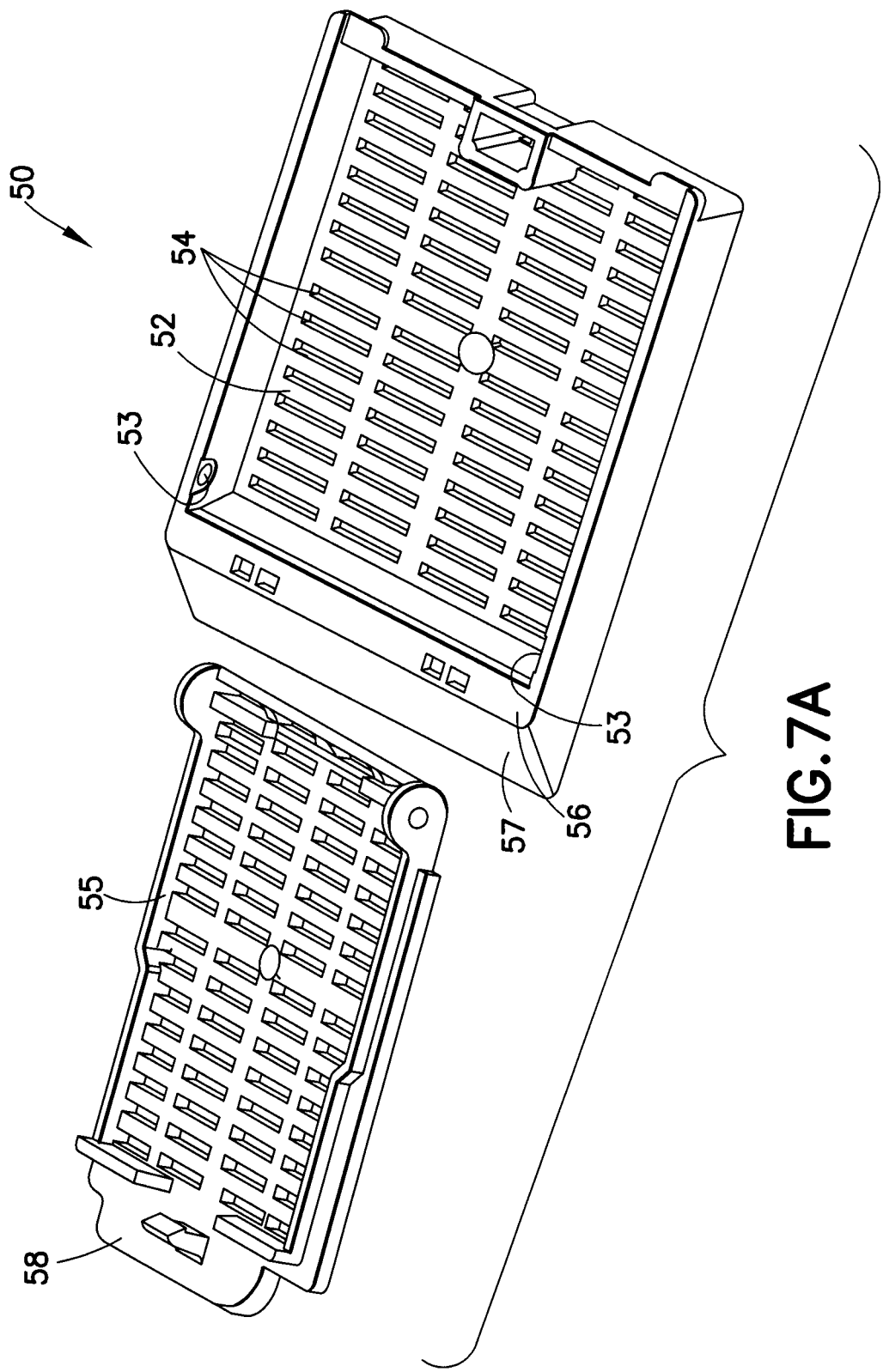
FIGS. 7A and 7B are perspective views of one embodiment of the sample holder, shown in an open and closed position, respectively.
Figure 7B:
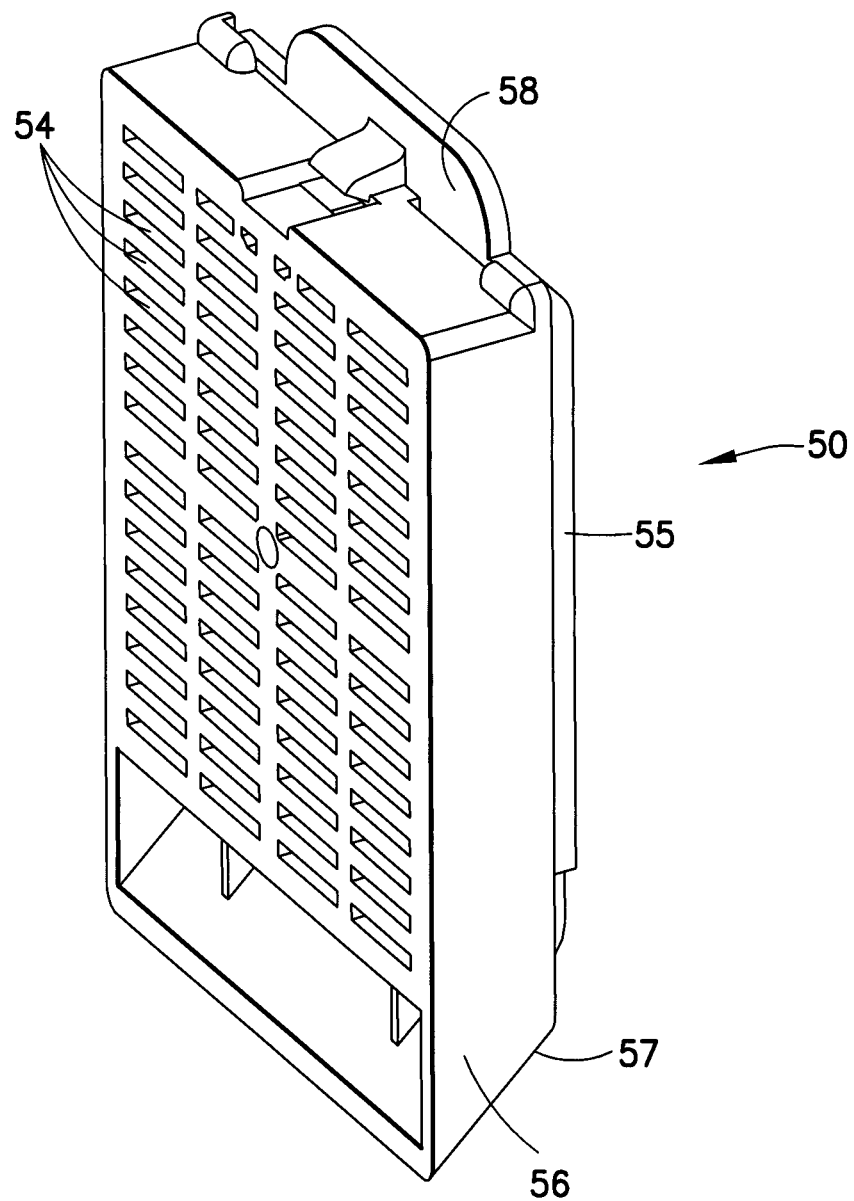

Referring to the drawings, in which like reference characters refer to the like parts throughout the several views thereof, FIG. 1 illustrates a container unit 10 in accordance with an embodiment of the present invention. Generally, container system or unit 10 includes a first container 12, a second container 32, a first closure 22, and a second closure 42. Container unit 10 is generally to be used in conjunction with a sample holder 50, an example of which is shown in FIGS. 7A and 7B. The individual components of container unit 10 may be made of any suitable material that is impervious to liquid and/or gas, such as glass and/or plastic. In one embodiment, first container 12 and second container 32 may be made of one or more than one of the following representative materials: polypropylene, polyethylene terephthalate (PET), glass, or combinations thereof.

Figure 2:
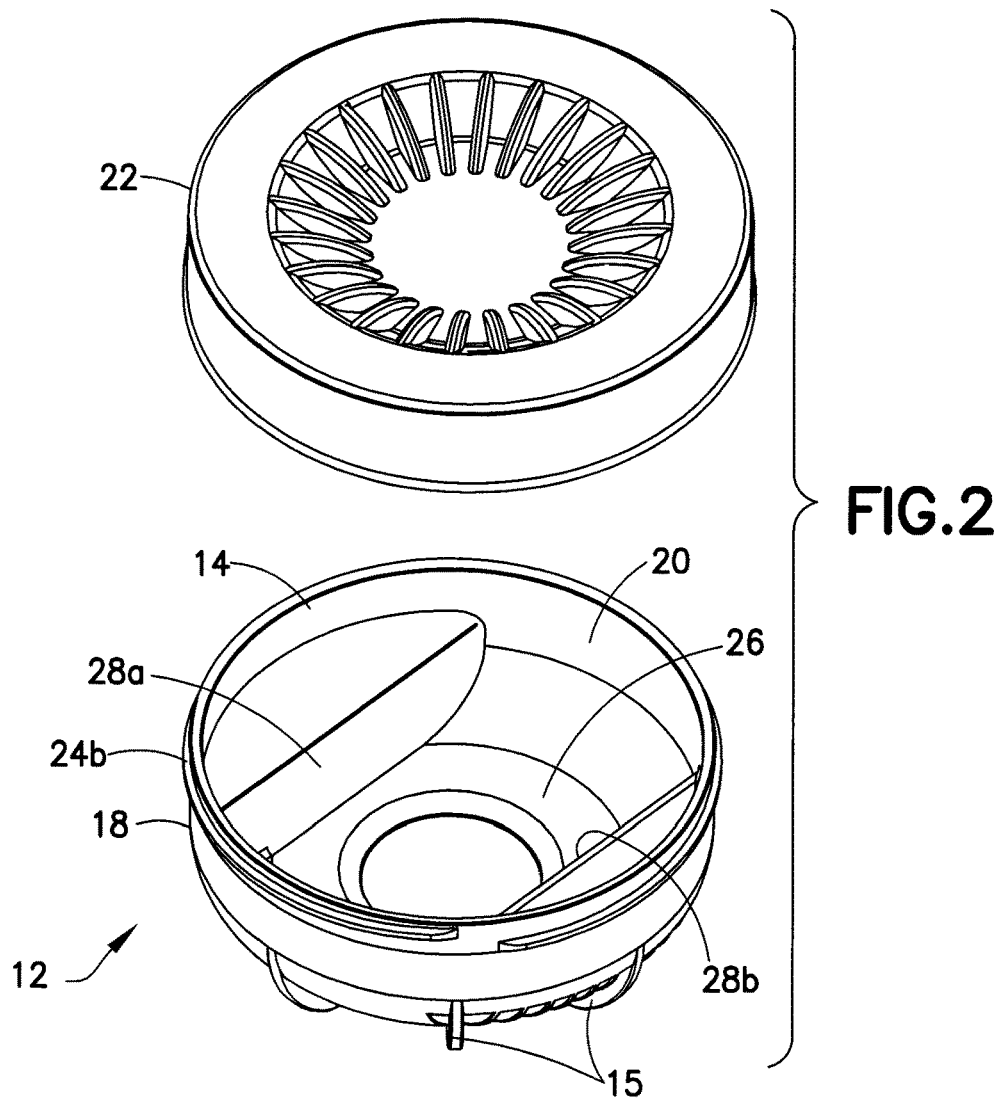
FIG. 2 is a perspective view of a first container and a first closure of the system of FIG. 1 showing the first container interior.
Figure 3:
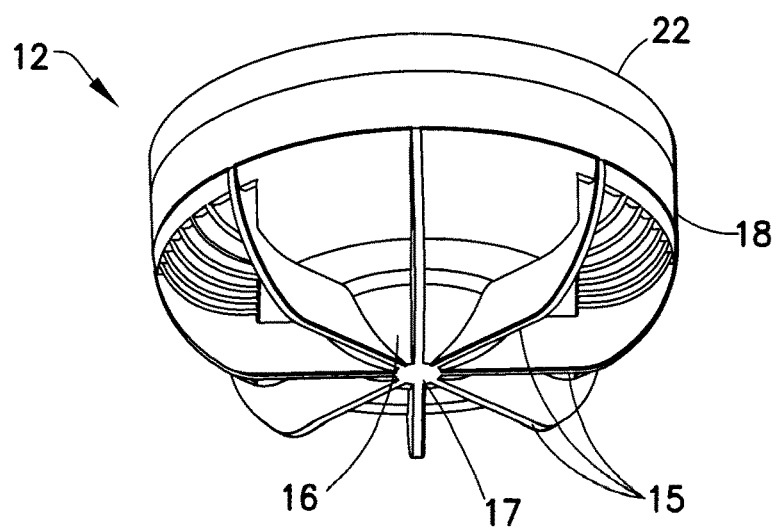
FIG. 3 is a bottom perspective view of the first container of the system of FIG. 1 with the first closure attached.
Figure 4:
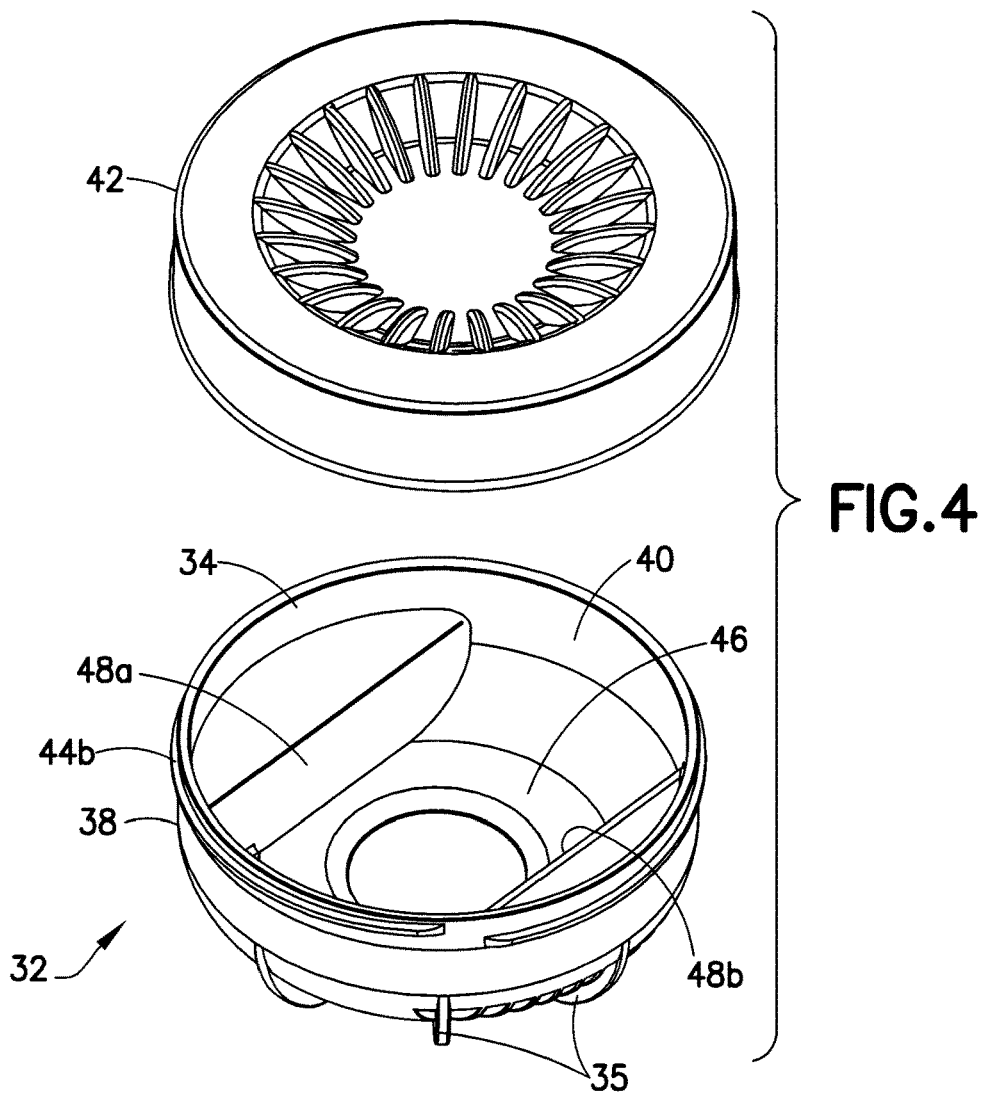
FIG. 4 is a perspective view of a second container and a second closure of the system of FIG. 1 showing the second container interior.
Figure 5:
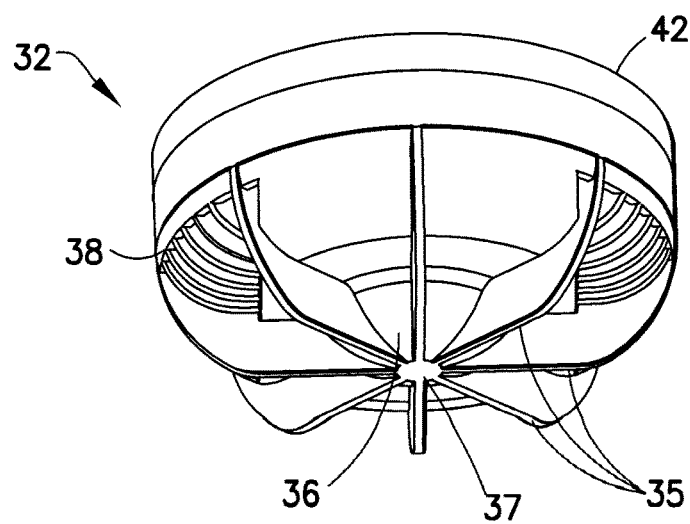
FIG. 5 is a bottom perspective view of the second container of the system of FIG. 1 with the second closure attached.
Figure 6:
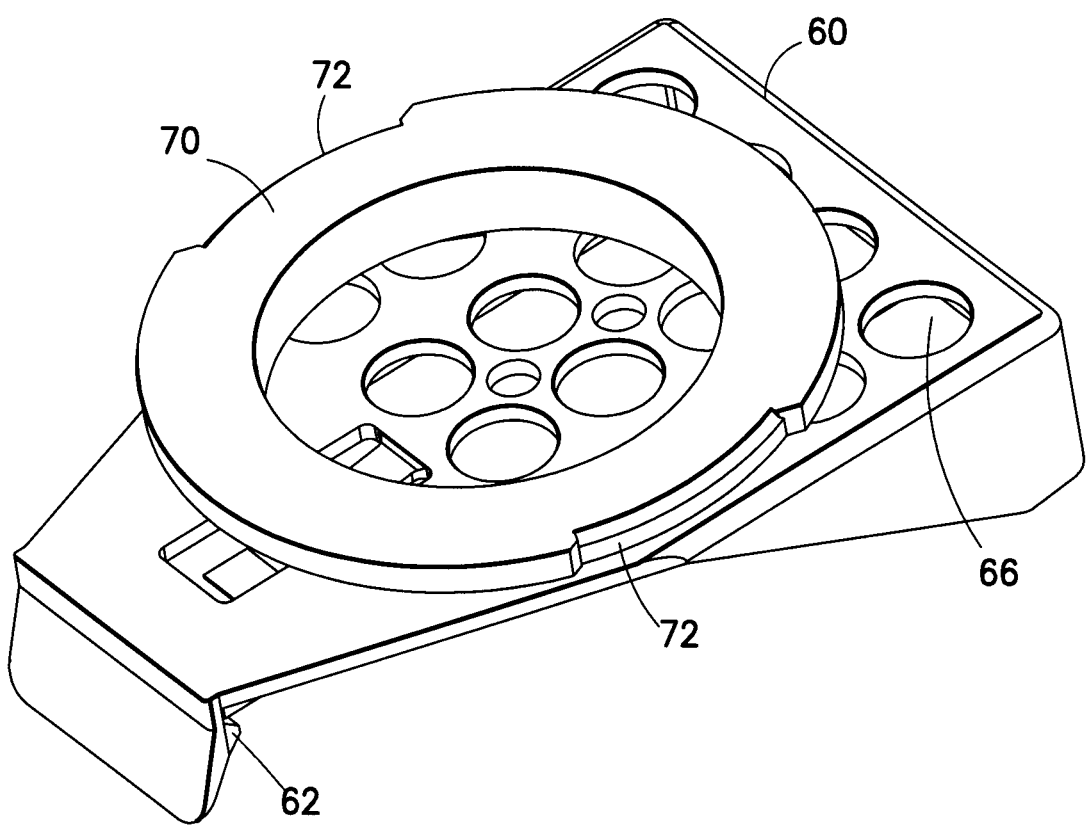
FIG. 6 is a perspective view of a platform for connecting a sample holder to the first closure in an embodiment of the invention.

First container 12, illustrated in FIGS. 2-3, generally includes an open end 14, a closed end 16, and a sidewall 18 extending between open end 14 and closed end 16 and defining a first container interior 20. Second container 32, shown in FIGS. 4-5, also generally includes an open end 34, a closed end 36, and a sidewall 38 extending between open end 34 and closed end 36 and defining a second container interior 40. First container interior 20 has a first intended fill volume, and is sized so as to receive and accommodate a sample holder 50 therein, as will be discussed in more detail. Additionally, first container interior 20 may include internal sidewall surfaces 28a and 28b, defining, along with closed end 16 and sidewall 18, a cavity 26 generally corresponding to the size and shape of sample holder 50. Second container interior 40 has a second intended fill volume, which may be different or equal to the first intended fill volume, and is sized so as to receive and accommodate therein the same sample holder 50 as is accommodated by first container interior 20. As with first container interior 20, second container interior 40 may also include internal sidewall surfaces 48a and 48b, defining, along with closed end 36 and sidewall 38, a cavity 46 generally corresponding to the size and shape of sample holder 50.

First container 12 may include a plurality of structural ribs 15 adjacent first closed end 16 on the external surface thereof. Ribs 15 may extend across first closed end 16, with a plurality of ribs 15 meeting at central point 17. Such ribs 15 provide structural integrity to first container 12, and provide a stable bottom surface for first container 12, with the plurality of ribs forming a generally planar surface for first container 12 so as to sit upright on a table. Moreover, such ribs 15 provide first container 12 with an overall dimension having such a stable bottom surface and being capable of ease of handling for a user, with an external profile for ease of handling while maintaining a reduced internal volume space so as to be able to maintain a sample holder 50 containing a tissue sample therein properly submerged in a liquid contained within the first container 12 in a minimal amount so as to prevent the use of excess reagents. Similarly, second container 32 may include a plurality of ribs 35 meeting at a central point 37, and any additional containers used in the container system may be similarly constructed.

Figure 9:
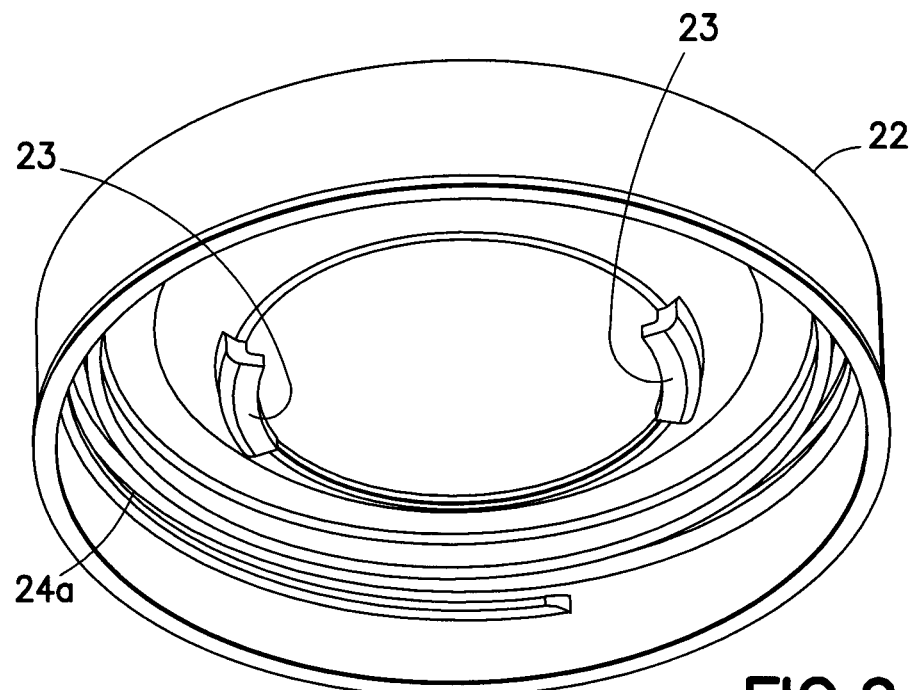
FIG. 9 is a bottom perspective view of the first closure FIG. 1 showing threaded members disposed thereon.
Figure 10:
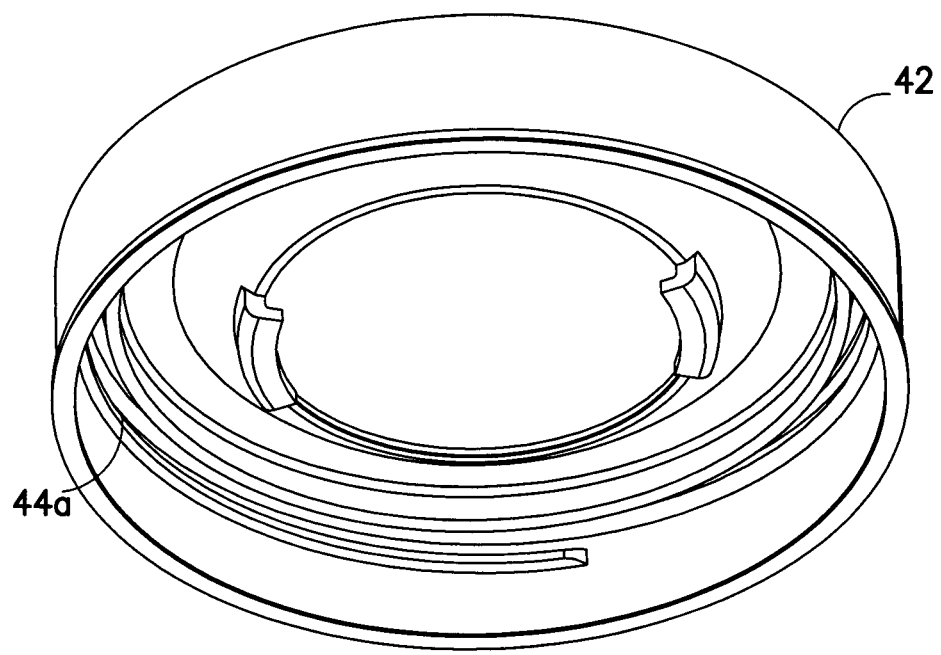
FIG. 10 is a bottom perspective view of the second closure FIG. 1 showing threaded members disposed thereon.
Figure 11C:
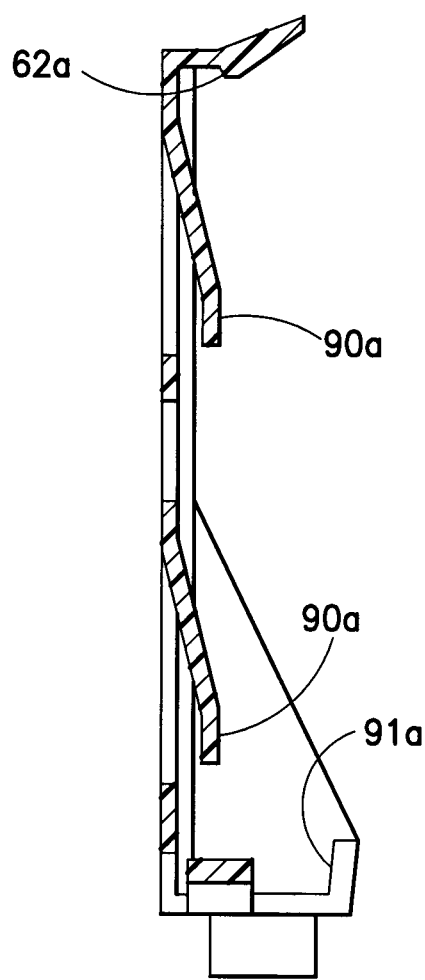
FIG. 11C is a side sectional view of the platform taken along line A-A of FIG. 11B.
Figure 11D:
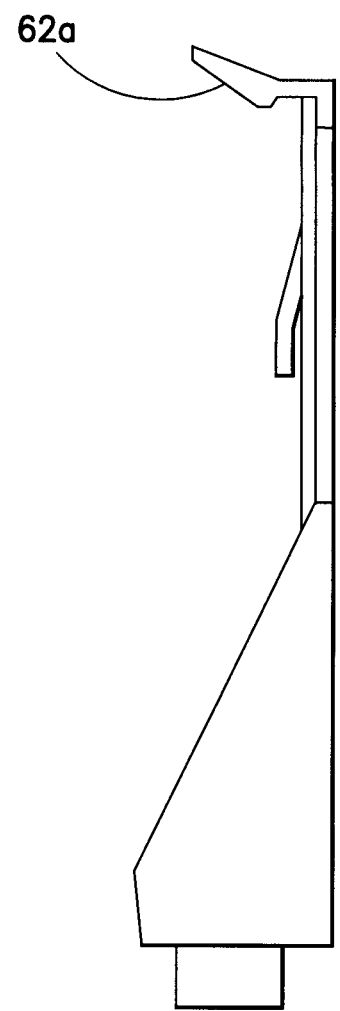
FIG. 11D is a side view of the platform of FIG. 11A.
Figure 11E:
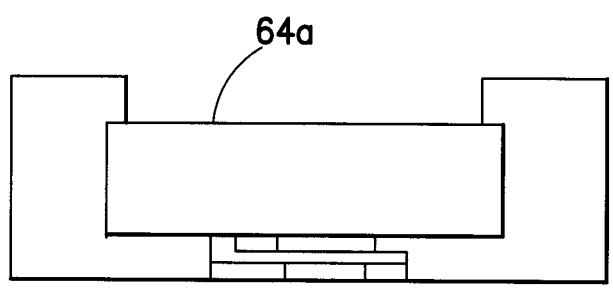
FIG. 11E is a top view of the platform of FIG. 11A.

Container unit 10 additionally includes a first closure 22, shown in FIG. 9, and a second closure 42, shown in FIG. 10, for enclosing first open end 14 and second open end 34, respectively. First closure 22 is matable with first container 12 and second closure 42 is matable with second container 32. First closure 22 may be matable with first container 12 in any manner, such as a frictional fit, snap fit, threadable engagement, interlocking structural engagement, or other manner, providing a liquid tight seal. Preferably, first closure 22 is threadably matable with first container 12 by way of a set of threaded members 24a and 24b, disposed on first closure 22 and first container 12, respectively. Alternatively, it is contemplated that corresponding threaded engagement may be provided through external threads on the outside of first closure 22 for engagement with internal threads on the interior surface of first container 12 within first sidewall at first open end 14. Second closure 42 may be matable with second container 32 in any manner, such as a frictional fit, snap fit, threadable engagement, interlocking structural engagement, or other manner, providing a liquid tight seal. In one embodiment, second closure 42 is threadably matable with second container 32 by way of a second set of threaded members 44a and 44b disposed on second closure 42 and second container 32, respectively. In another embodiment, the second closure is a removable membrane, such as a peel away foil or wax material that is affixed to, second open end 34 of second container 32.

In one particular embodiment, first closure 22 is also matable with second container 32 so that, when mated, first closure 22 encloses second open end 34 of second container 32. Accordingly, first closure 22 can be transferred from first container 12 to second container 32, thereby providing a mechanism for transferring sample holder 50 from first container 12 to second container 32, as will be discussed in further detail. While first closure 22 is matable with second container 32 by any manner capable of providing a liquid seal, preferably first closure 22 is threadably matable with second container 32. In this arrangement, first closure 22 mates with second container 32 through the engagement of threaded member 24a on first closure 22 with threaded member 44b on second container 32.

Container unit 10 is intended to be used in conjunction with a sample holder 50 in order to treat a biological sample housed within sample holder 50. Sample holder 50 is adapted to be received within first container 12. Sample holder 50 may be in the form of a conventional histology cassette (a "histo-cassette") as is known in the art for storing a biological tissue sample during preparation of the sample for diagnostic testing. Such sample holders or histo-cassettes are known for containing biological specimens during processing with fluids to prepare the specimen for later analyses. Typically, such sample holders or histo-cassettes are generally rectangular, planar housing structures having an internal cavity, with a plurality of openings through the wall surface to provide fluid flow through the housing. Often, a removable or openable cover encloses the structure, such as through a hinge situated along one end of the housing structure for providing a door-like cover to the housing structure. Also, a planar surface, which may be slanted, is often provided in such sample holders or histo-cassettes, acting as a surface for labeling or writing. The dimensions for such a sample holder, for example, may include a height of about 0.3 inch (plus or minus 0.1 inch), a length of about 1.73 inches (plus or minus 0.1 inch), and a width of about 1.12 inches (plus or minus 0.1 inch). Examples of sample holders that may be useful herein are shown in U.S. Pat. No. 4,220,252 to Beall et al. and U.S. Pat. No. 4,034,884 to White, both of which are expressly incorporated herein by reference.

For example, as shown in FIGS. 7A and 7B, sample holder 50 includes a generally rectangular planar housing 56 having opposing walls defining an internal cavity 52 for holding a biological tissue sample therein. At least one of the walls of housing 56 may be slanted, such as slanted wall 57, providing a surface for applying a label or for writing, so as to provide a mechanism for identification of a sample contained within sample holder 50, as appropriate. Housing 56 of sample holder 50 is a closable structure, and may include a hinged door-like structure 55 attached with housing 56 thereby permitting access to the internal cavity 52 for storing a tissue sample within or removing a tissue sample from internal cavity 52. The door-like structure 55 may be integrally formed with housing 56 so as to provide a unitary structure with the door-like structure 55 connected to housing 56 through a flap to provide a mechanism for pivoting door-like structure 55 with respect to housing 56. Alternatively, the hinged door-like structure 55, may be connectable to housing 56, such as through a pivot point 53 acting as a hinge for opening door-like structure 55 from one side of housing 56 to gain access to the internal cavity 52. Housing 56 of sample holder 50 includes at least one, and preferably a plurality of fluid openings 54 adapted to allow fluid to flow therethrough. In this manner, when housing 56 is positioned within first container 12, fluid within first container 12 can flow through openings 54 and contact the biological tissue sample contained within internal cavity 52.

Figure 8:
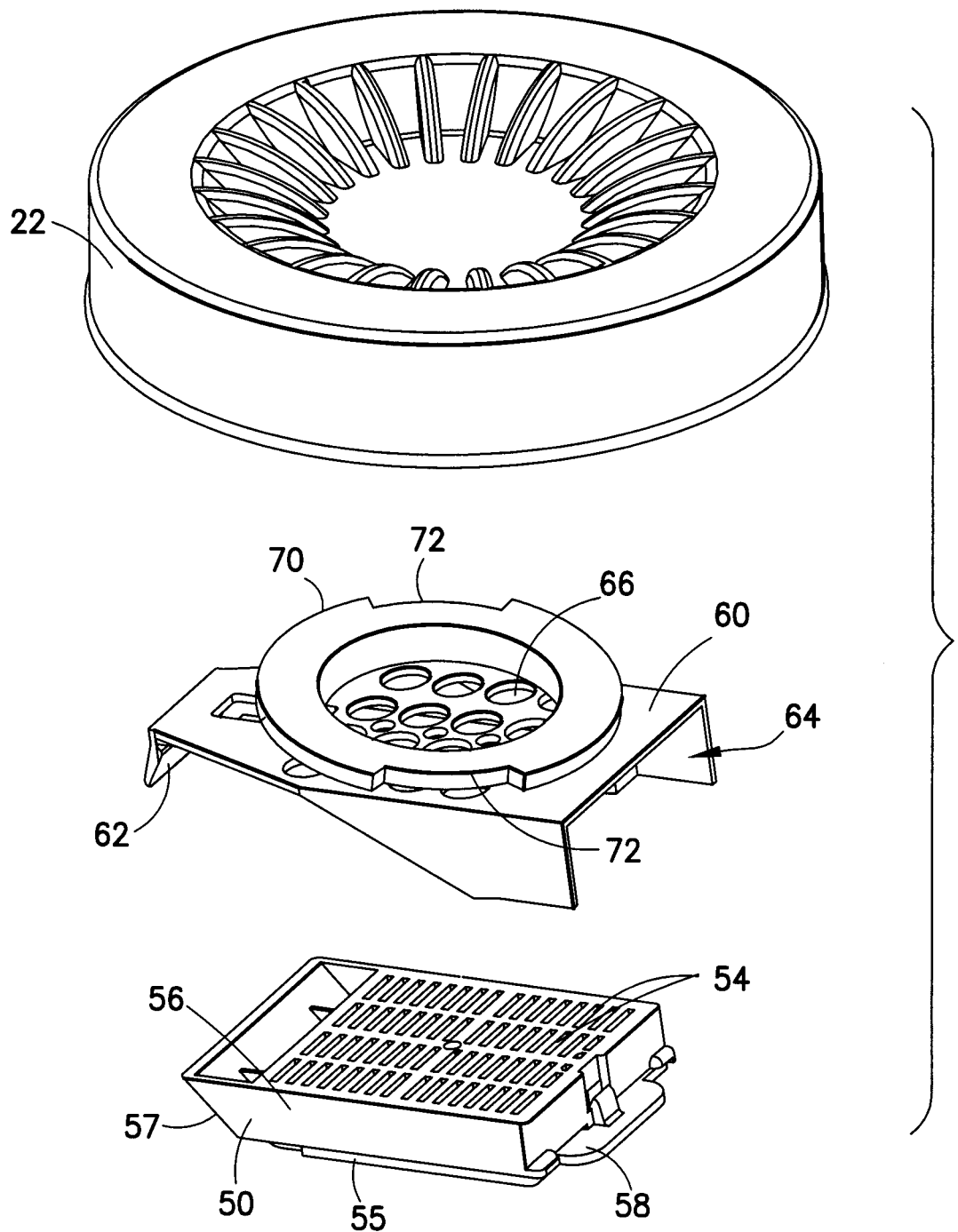
FIG. 8 is an exploded view of the first closure of FIG. 1, where a sample holder is rotatably connected to the first closure by way of the platform and a pivoting connection.

As noted, sample holder 50 may be provided as a separate element for use within first container 12, or may be interconnected with a part of container 10. Desirably, sample holder 50 is mated with first closure 22. Such mating may be accomplished by providing sample holder 50 as an integral part connected to or formed with first closure 22, or sample holder 50 may be a separate structure that is removably matable or detachably connected with first closure 22. As shown in FIG. 8, first closure 22 may include a platform 60 extending from a bottom surface of first closure 22, for accommodating sample holder 50 therein. Platform 60 may include structure for maintaining sample holder 50 attached to first closure 22, such as in a snap-fit engagement, and sample holder 50 may be releasable from platform 60. In particular, platform 60 may be a structure defining a rectangular recess for accommodating the general size and shape of sample holder 50. Platform 60 may include at least one finger 62 extending therefrom for engaging with sample holder 50, thereby maintaining sample holder 50 within the recess defined by platform 60. Such finger 62 may be deflectable, such that when an edge of sample holder 50 is held in place against a corresponding wall surface of the platform 60, and sample holder 50 is pushed into the recess of platform 60, finger 62 deflects away from the wall of sample holder 50 and then returns to an initial position, thereby snapping sample holder 50 in place against an edge of slanted wall 57. Finger 62 may lock sample holder 50 in place permanently with respect to platform 60 and first closure 22, or may be deflectable so as to remove sample holder 50 from platform 60 if desired.

Platform 60 may also be provided with a general shape so as to permit opening of door 55 of sample holder 50 while maintaining housing 56 of sample holder 50 contained therein, thereby providing access to the interior cavity 52 of sample holder 50 while sample holder 50 is held in place within platform 60 and with respect to first closure 22. For example, platform 60 may have a wall cut-away portion 64 to accommodate a handle-like protrusion 58 of door 55, and the overall dimensions and height of the walls of platform 60 may be designed so as to provide for manually opening of the door 55 by contact of handle 58 and pivoting of door 55 across platform 60 without interference. Platform 60 may also include a plurality of holes 66 to allow fluid to pass through platform 60 to contact the sample holder 50 and the sample contained therein.

In one embodiment, the platform may include structure making it capable of accommodating histo-cassettes or sample holders of different sizes and shapes. For example, as shown in an alternative embodiment depicted in FIGS. 11A-11E, platform 60a may include fingers 90a and 92a, which act as compressible elements for bearing against the wall surfaces of sample holders of various sizes. Such fingers 90a and 92a may act as biasing elements or leaf springs for exerting a biasing force against the wall surface of a sample holder placed within platform 60a, biasing the sample holder against the sidewalls of platform 60a to hold the sample holder in place. More particularly, fingers 90a apply a biasing force against a sample holder contained within platform 60a, while opposing surface 91a holds an end of the sample holder therein and finger or protrusion 62a holds a separate edge of the sample holder therein. Also, finger 92a applies a biasing force against the sample holder while opposing protrusion 62a holds the end of the sample holder in place. Such opposite and equal forces assist in maintaining sample holders of various sizes and shapes in place. Further, wall cut-away portion 64a may also be provided, for accommodating a handle portion of the door of the sample holder, as discussed above, while also providing access to the handle portion for opening of the door while the sample holder is in place in the platform, if desired. In this manner, container unit 10 may be provided with a single platform that can accommodate various sizes and shapes of histo-cassettes therein for use with container unit 10. Additionally, platform 60a may include a plurality of holes 66a for fluid flow therethrough, as discussed above. Such holes 66a may include a pattern or orientation such that fluid flow through the platform to the sample holder will be sufficient for contact with a sample contained within the sample holder regardless of the size, shape and/or geometry of the sample holder.

In one embodiment, sample holder 50 is rotatably engaged with first closure 22 such that sample holder 50 rotates with respect to first closure 22. This may be accomplished, for example, by providing platform 60 as a structure which is rotatable with respect to first closure 22, such as through a pivoting connection established through ring 70, and by providing sample holder 50 within platform 60. This arrangement is shown in FIG. 8. In particular, ring 70 may represent a generally circular structure that is adapted for engagement with corresponding structure on the underside surface of first closure 22. This may be accomplished by providing first closure 22 with at least one, and desirably a plurality of tabs 23 for accommodating ring 70 in a rotational engagement therewith. Tabs 23 are desirably spaced in an opposing manner from each other to define a perimetrically rotational area on the underside surface of closure 22. Ring 70 is adapted to fit within the rotational area defined by tabs 23, so as to provide a rotational engagement between ring 70 (and therefore platform 60 and sample holder 50 connected thereto) and first closure 22.

Ring 70 may also include at least one, and desirably a plurality of notches 72 about a perimeter of ring 70, designed to align with tabs 23 of first closure 22 during assembly. Desirably, ring 70 includes the same number of notches 72 to correspond with the number of tabs 23 on the first closure 22. Notches 72 may be aligned with tabs 23 during assembly, with ring 70 pushed down within the area defined by tabs 23. The outer circumference of ring 70 at the location of notches 72 has a diameter which is slightly larger than the inner diameter of the area defined between tabs 23, such that alignment of ring 70 requires pushing down of the ring 70 with notches 72 between the tabs 23 to cause a slight interference fit of ring 70 and a slight snap fit engagement. Such interfitting provides a mechanism for attachment of ring 70 to first closure 22 in a rotatable manner such that ring 70 cannot be removed from closure 22 unless notches 72 are aligned with tabs 23 and force is used to pull the ring 70 from the closure 22.

Such interfitting of ring 70 within the area defined by tabs 23 provides a rotational connection between platform 60 and first closure 22. In this manner, when sample holder 50 is placed within first container 12 or second container 32 and sample holder 50 is rotatably engaged with first closure 22 such as for threadably attaching it thereto, one or both of platform 60 and/or sample holder 50 will contact one or more of the internal sidewall surfaces 28a, 28b or 48a, 48b upon rotation of first closure 22, thereby maintaining sample holder 50 in place within cavity of first container 26 or cavity 46 of second container 32. This arrangement is advantageous in that it allows first closure 22 to be threadably mated to first container 12 and/or second container 32 while sample holder 50, and the biological sample included therein, remain stationary within the container interior during the mating process. Moreover, first closure 22 and first container 12 have an engagement position and a disengagement position, such as is provided through threaded engagement discussed above, so as to have a rotational positioning of closure 22 with respect to first container 12 wherein first closure 22 is attached to or unattached from first container 12. In order to ensure proper orientation, first closure 22 may include an orientation such that platform 60 must be properly aligned within the cavity of first container 26 prior to movement of the first closure 22 from the disengagement position where it is not engaged with first container 12 to the engagement position where it is engaged with first container 12 and attached thereto. The rotation of platform 60 with respect to first closure 22 provides for such alignment and engagement to the engaged position. In one configuration, the first closure 22 is transitionable from a disengagement position in which the first closure 22 is disengaged from the open end 14 of the first container 12, to an engagement position in which the first closure 22 encloses the open end 14 of the first container 12. In order to allow transition of the first closure 22 from the disengagement position to the engagement position, the platform 60 must be aligned with the sample holder cavity of the container interior 20, such that unobstructed entry of the platform 60 into the sample holder cavity of the container interior 20 is possible. In a further configuration, the orientation of the platform 60 with respect to the container interior 20 remains substantially fixed during rotation of the first closure 22 with respect to the first container 12.

Another aspect of container unit 10 relates differentiating between first container 12 and second container 32. This is best accomplished by way of a visual indicator or indicators 67 disposed on at least one of the containers. The indicator 67 can be disposed at any position on either first container 12 or second container 32 that is visible to user. In one embodiment, an indicator 67 is disposed on first closure 22. In another embodiment, an indicator 67 is disposed on second closure 42. The indicator 67 could also be disposed on sidewall of either first container 12 or second container 32. As examples, the indicator 67 can be in the form of a numeral, a line or series of lines, or a color. The indicator 67 could also be integrated into a membrane covering second open end 34 of second container 32. In another embodiment, first container 12 is formed from a colored material while second container 32 is formed from a different colored material.

First container interior 20 and second container interior 40 are dimensioned so that they can sequentially receive the same sample holder 50 therein. The benefit of this arrangement allows a user to transfer sample holder 50 from first container interior 20 to second container interior 40. Moreover, by providing sample holder 50 connected with first closure 22, first closure 22 can be removed from first container 12 and thereafter sequentially attached to second container 32 (and any additional containers as well), thereby requiring only one closure for containing sample holder 50 for suspension within first container 12, second container 32, and any other number of sequential containers.

As previously mentioned, first container interior 20 and second container interior 40 may contain a first medium and a second medium, respectively. In one embodiment, first container interior 20 is empty and acts as a housing or staging space for sample holder 50 before sample holder 50 is inserted into second container interior 40. In another embodiment, first container interior 20 contains a first reagent and second container interior 40 contains a second reagent, where the first reagent is different than the second reagent. Container unit 10 may be assembled and provided with liquid media, such as solutions or reagents, stored within first container 12 and/or second container 32 at the point of manufacture. Alternatively, any such liquid media may be filled into the first container 12 and/or the second container 32 at any point prior to use, such as directly prior to inserting a tissue sample into sample holder 50.

More particularly, container unit 10 may be provided for use with a one reagent system. In this manner, a single reagent solution, such as a tissue fixative like formalin, may be provided within second container 32. Such fixative solutions stabilize the RNA within a tissue sample, for conducting molecular diagnostic testing. Alternatively, container unit 10 may be provided for use with a two solution or a two reagent system. For example, a wash solution may be provided in second container 32, so as to wash the first reagent fixative from the sample holder 50 after it is submersed therein while in the first container 12. It is also possible that each container contains the same reagent since it may be advantageous to refresh the same reagent after a period of time has passed. Or, a first reagent solution, such as a tissue fixative like formalin, may be used within first container 12, and a second reagent solution, such as a stabilizer in the form of a nucleic acid stabilization reagent for stabilizing the morphology of the tissue sample, may be provided within second container 32.

Any reagents may be used with the container of the present invention. For example, the fixative may be formalin, ethanol solutions, Carnoy's solution I (ethanol and acetic acid), Carnoy's Solution II (ethanol, chloroform and acetic acid), methacarn (methanol, chloroform and acetic acid), Clark's fixative, Boonfix, and the like. A non-limiting list of commercially available fixatives includes, but is not limited to, MIRSKY'S FIXATIVE (available from National Diagnostics, Inc. of Atlanta, Ga.); GLYOFIX (available from Shandon Lipshaw, Inc. of Pittsburgh, Pa.); HISTOCHOICE® (available from Amresco); HISTOFIX (available from Trend Scientific, New Brighton, Minn.); KRYOFIX® (available from Merck); MICROFIX (available from Energy Beam Sciences, Inc., East Granbury, Conn.); NEOFIX (available from Merck); NOTOX (available from Earth Safe Industries, Inc., Belle Mead, N.J.); OMNIFIX II and OMNIFIX 2000 (available from AnCon Genetics, Inc, Mellville, N.Y.); PREFER (available from Anatech Ltd, Battle Creek, Mich.); PRESERVE (available from Energy Beam Sciences, Inc., East Granbury, Conn.); SAFEFIX II (available from Thermo Fischer Scientific, Inc.); STATFIX (available from StatLab Medical Products, Inc. of Lewisville, Tex.); S.T.F.® (available from Streck Laboratories, Omaha, Neb.); UMFIX (available from Sakura Finetek USA, Inc., Torrance, Calif.); and FINEFIX (available from Milestone Medical of Shelton, Conn.). Commercially available stabilizers include, but are not limited to, RNALATER® (available from Ambion, Inc., Austin Tex.); and RNEASY (available from Qiagen, Inc., Valencia, Calif.). Any other reagents known or hereafter discovered for use as fixatives and/or stabilizers are intended as useful in the present invention.

The container unit 10 can be sold as a kit of parts including first container 12, second container 32, first closure 22, and second closure 42. In this arrangement, the user may decide which solution or solutions to put in the respective containers. Alternatively, container unit 10 may be sold as part of a more complete system for preserving a biological sample, which also includes a first solution disposed in first container 12 and/or a second solution disposed in second container 32. In this embodiment, the second solution may be the same as or different than the first solution.

The primary method of using container unit 10 involves placing the desired biological sample into sample holder 50, as would be understood by one skilled in the art, and then inserting sample holder 50 into first container interior 20, such as by attaching first closure 22 to first container 12 with sample holder 50 attached to first closure 22. This may be accomplished by aligning the platform 60 with sample holder 50 attached thereto over the sample holder cavity established by sidewalls surfaces 28a, 28b within cavity 26, and rotating first closure 22 with respect to first container 12, thereby causing first closure 22 to engage with first container 12, such as through threaded engagement, while platform 60 rotates with respect to first closure 22 to maintain sample holder within cavity 26 with little or no rotational movement thereof. In doing so, the tissue sample container within sample holder 50 is placed in contact with any fluid contained within first container 12, such as a first reagent. After the biological tissue sample has had sufficient contact with the reagent in first container interior 20, the user transfers sample holder 50 from first chamber interior 20 to second chamber interior 40. This is accomplished by transferring first closure 22 from first container 12 to second container 32, after removing second closure 42 (which may be a removable membrane) therefrom. With first closure 22 now attached to second container 32, the sample holder 50 including the tissue sample is placed in contact with the second container interior 40, which may also contain a reagent, and preferably is a different reagent than within first container 12. With sample holder 50 mated with first closure 22, the user does not come in direct contact with sample holder 50 after it is mated with first closure 22, but instead only contacts first closure 22 during the transfer of sample holder 50 between first container interior 20 and second container interior 40. This feature helps avoid potential contamination of the biological sample during the preservation process.

While embodiments of the present invention are satisfied in many different forms, there is shown in the figures and described herein in detail, specific embodiments of the invention, with the understanding that the present disclosure is to be considered as exemplary of the principles of the invention and is not intended to limit the invention to the embodiments illustrated. Various other embodiments will be apparent to, and readily made by those skilled in the art, without departing from the scope and spirit of the invention. For example, while the present disclosure generally discusses a two container system, it is contemplated that embodiments of the system may include other numbers of containers, such as three or four, for accommodating varying reagents therein. The scope of the invention will be measured by the appended claims and their equivalents.

What is claimed is:

1. A system for storing and preserving a biological sample, comprising:
   a first container having a closed end, an open end, and a sidewall extending between the closed end and the open end defining a first container interior;
   a second container having a closed end, an open end, and a sidewall extending between the closed end and the open end defining a second container interior;
   a first closure for enclosing the open end of the first container, wherein the first closure has a bottom surface detachably connectable to a sample holder having an internal cavity configured for holding a biological sample; and
   a second closure for enclosing the open end of the second container,
   wherein the first closure is adapted to dispose the sample holder within the first container interior when the first closure encloses the open end of the first container, and the first closure is adapted to subsequently dispose the sample holder within the second container interior when the first closure encloses the open end of the second container,
   wherein the first closure is rotatable with respect to the sample holder when the sample holder is connected to the first closure and when the first closure encloses the open end of the first container or the second container such that an orientation of the sample holder remains substantially fixed relative to the first container or the second container during rotation of the first closure relative to the first container or the second container, and
   wherein the sample holder comprises a closable housing comprising a plurality of fluid openings adapted for allowing fluid contained within at least one of the first container and the second container to pass into the internal cavity.

2. The system of claim 1, further comprising a first solution disposed within the first container, and a second solution disposed within the second container, the second solution being different than the first solution.

3. The system of claim 1, wherein the sample holder is a histology cassette.

4. The system of claim 1, wherein at least a portion of the first closure and at least a portion of the first container are adapted for threaded engagement therebetween.

5. The system of claim 1, wherein at least a portion of the first closure and at least a portion of the second container are adapted for threaded engagement therebetween.

6. The system of claim 1, wherein at least one of the first container and the second container comprises a visual indicator to differentiate the first container from the second container.

7. The system of claim 1, wherein the interior of the first container defines a first intended fill volume and the interior of the second container defines a second intended fill volume, the second intended fill volume being different from the first intended fill volume.

8. The system of claim 1, wherein the second closure is a removable membrane.

\* \* \* \* \*